United States Patent [19]

Pomponi et al.

[11] Patent Number: 5,446,207

[45] Date of Patent: Aug. 29, 1995

[54] ANTI-DYSLIPIDEMIC AGENTS

[75] Inventors: Shirley A. Pomponi, Forth Pierce, Fla.; Vincent P. Gullo, Liberty Corner, N.J.; Ann C. Horan, Summit, N.J.; Mahesh G. Patel, Verona, N.J.; Stephen J. Coval, Clinton, N.J.

[73] Assignee: Harbor Branch Oceanographic Institution, Inc., Fort Pierce, Fla.

[21] Appl. No.: 115,947

[22] Filed: Sep. 1, 1993

[51] Int. Cl.6 .............................. C07C 43/23
[52] U.S. Cl. .................................... 568/633
[58] Field of Search ........................ 568/633

[56] References Cited

FOREIGN PATENT DOCUMENTS 0476493  3/1992  European Pat. Off. ............ 514/719
0516082  5/1992  European Pat. Off. ............ 514/719

OTHER PUBLICATIONS

Bulletin of the Chemical Society of Japan vol. 52, No. 2, Feb., 1979, pp. 629–630.
JOC, vol. 51, No. 24, 28 Nov. 1986, pp. 45 68–4573 Sullivan, et al.
Studies on the Fauna of Curacao and Other Caribbean Islands, 62 (191): pp. 69–71 (1980).
Journal of Natural Products, vol. 54, No. 4, pp. 1108–1111, Jul.–Aug. (1991).
Tetrahedron, vol. 35, pp. 609–612 (1979).
Pure and Applied Chem., vol. 51, pp. 1893–1900 (1979).

Primary Examiner—James H. Reamer
Attorney, Agent, or Firm—James R. Nelson; Eric S. Dicker; Matthew Boxer

[57] ABSTRACT

Compounds of the formula:

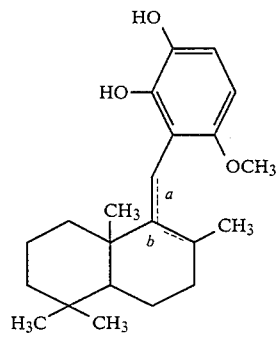

I wherein a is a single bond and b is a double bond; or a is a double bond and b is a single bond; and enantiomers thereof; or a pharmaceutically acceptable salt thereof are described. These compounds can improve lipoprotein profile of dyslipidemic patients and generate an anti-atherogenic lipoprotein profile of normolipidemic individuals. In addition, inhibition of CETP activity may be useful as anti-fertility agents.

4 Claims, No Drawings

ANTI-DYSLIPIDEMIC AGENTS

BRIEF SUMMARY OF THE INVENTION

The invention relates to compounds of the formula:

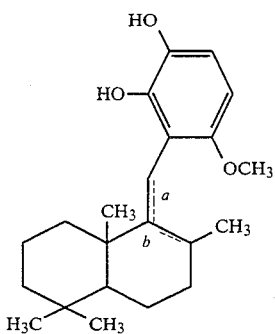

I wherein a is a single bond and b is a double bond; or a is a double bond and b is a single bond; and enantiomers thereof; or a pharmaceutically acceptable salt thereof.

The compounds of the invention can be written as individual structures as follows:

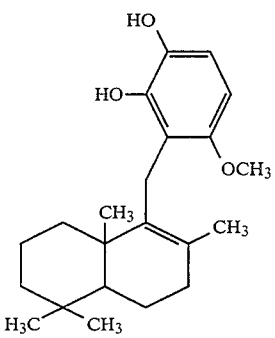

A and as

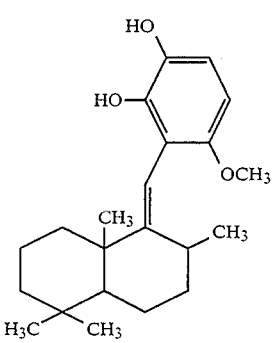

B

More specifically, the compounds of the invention can be written as:

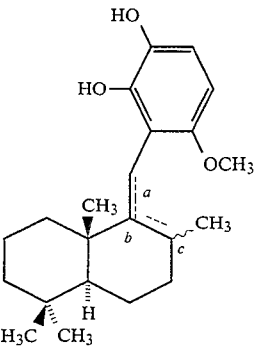

I' wherein a is a single bond, b is a double bond and c is a single bond that is in the plane of the page; or a is a double bond, b is a single bond and c is a single bond that is above the plane of the page; or a pharmaceutically acceptable salt thereof.

The compounds of the invention can be written as individual structures as follows:

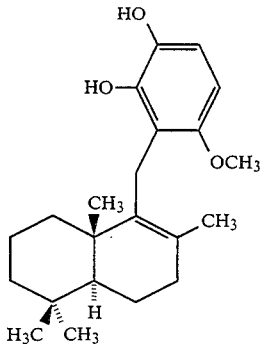

A' and

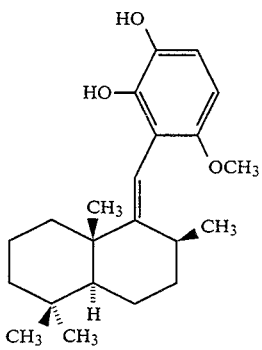

B' and have been given the trivial names wiedendiol-A (A) and wiedendiol-B (B).

In the structures shown just above, more of the stereochemistry of the chemical bonds are shown than in the flat formulas given ealier in the specification. In the structures shown just above, only the relative streochemistry for the compounds is known. The absolute stereochemistry for these compounds is not known. This point regarding relative and absolute stereochemistry is described in more detail below.

Atherosclerotic coronary artery disease (CAD) is the major cause of mortality in the United States and in the Western countries. One of the major reasons for developing CAD can be related to anabnormal lipoprotein profile. High serum cholesterol levels or high low density lipoprotein (LDL) cholesterol levels are a major risk factor for the disease. Recently, high density lipoprotein (HDL) cholesterol level have been found to be inversely correlated with CAD. HDL has also been to be found more strongly correlated with CAD than LDL. Finally, HDL has also been independently correlated with CAD, that is, whether or not you have high LDL. Castelll, W. P. et al (1986) JAMA 256, P2835-2838 and Gordon, D. J. et al (89) Circulation 79, P 8-15.

Several factors have been identified as modifying factors of LDL and HDL. Among them, cholesteryl ester transfer protein (CETP) also known as LTP-I, is one that directly modifies the lipoproteins, especially HDL. CETP is a plasma glycoprotein with molecular weight about 70,000 dalton and it transfers cholesteryl ester from HDL to triglyceride rich lipoproteins such as LDL Glomset, J. A.,(1968) J. Lipid Res. 9, 155–167 and Morton, R. E., and Zilversmit, D. B. (1979) J. Lipid Res. 23, 1058–1967.

In families with CETP deficiency, HDL levels were inversely correlated with the plasma CETP concentration and LDL levels were reduced, and the family members are generally long lived Inazu, A., et al. (1990) N. Eng. J. of Med 323, p1234–1238 and Brown, M. L., et al. (1989) and Nature 342, p448–451. On the other hand, mice that were genetically manipulated to possess human CETP in the plasma showed decreased HDL cholesterol level Agelion, L., et al. (1991) J. Biol. Chem. 266, p10796–10801. Studies also showed that inhibition of CETP activity in animals with inhibitory antibody greatly increased HDL levels Whitlock, M. E., et al. (1989) J. Clin. Invest. 84, p129–137. The lipid transfer activity associated with LTP-I was also found to support sperm capacitation Ravnik, S. E., et al. (1993) Fertility and Sterility 59. p629–638. Results of these studies and others suggest that inhibition of plasma CETP activity can improve lipoprotein profile of dyslipidemic patients and generate an anti-atherogenic lipoprotein profile of normolipidemic individuals. In addition, inhibition of CETP activity may be useful as anti-fertility agents for males and females.

These compounds (A and B) are active in the cholesteryl ester transfer protein (CETP) assay described below, and therefore can improve the lipoprotein profile of dyslipidemic patients and generate an atherogenic lipoprotein profile of normolipidemic. In addition, inhibition of CETP activity may be useful as anti-fertility agents.

The invention also relates to compositions which comprise a compound of formula I, that is, A or B, and a pharmaceutically active carrier material.

The invention also relates to a method for treating a mammal afflicted with dyslipidemia which comprises administering an effective amount of a compound of formula A or B. The invention also relates to a method for reducing the fertility of a mammal which comprises administering an anti-fertility effective amount of a compound of formula A or B as an anti-fertility agent The invention also comprises a method for preparing a compound of formula A or B, by extraction from the marine sponge Xestospongia cf. wiedenmayeri.

DETAILED DESCRIPTION OF THE INVENTION

As used herein, a boldfaced line ━ denotes a bond that is above the plane of the page. A dashed line ⦀ denotes a bond that is below the plane of the page. A straight line denotes a bond that is either within the plane of the page, or whose stereochemistry is not specified. A wavy line ∼ denotes a bond whose stereochemistry is not specified.

The following is a description of the preparation of compounds of formula A and B.

DESCRIPTION OF THE MARINE SPONGE

The compounds of the invention were extracted from a marine sponge which has the taxonomic identification Xestospongia cf. wiedenmayeri van Soest, 1980 (Phylum Porifera, Class Demospongiae, Order Haplosclerida, Family Petrosiidae). The sponge was collected by the Harbor Branch Oceanographic Institution, Inc of Fort Pierce, Fla. and given the sample number HRB 934 (HBOI/DMBR 2-VII-87-5-002). The sponge was collected by scuba diving at a depth of 37 meters from the fore reef escarpment off northwest Crooked Insland, Bahamas (latitude 22° 49.30'N, longitude 74°21.50'W). It was common in occurrence. The sponge was thickly encrusting to massive in morphology. The color in lefe was pinkish-tan externally, tan internally; in ethanol. it is reddish brown. The sponge is brittle, fragile, and crumbly in life. After collection, a subsample of the sponge was preserved in ethanol as a taxonomic voucher; the remainder of the sponge was stored frozen at $-20°$ C. The voucher specimen is currently deposited at Harbor Branch Oceanographic Museum, catalog number 003:00073. It is preserved in 70% ethanol with an expected shelf life of at least 30 years and is accessible to those skilled in the art for taxonomic identification purposes.

The description of Xestosoongia cf. wiedenmaveri can be found in van Soest, R. W. M. 1980. Marine sponges from Curacao and other Caribbean localities. Part II. Haplosclerida. *Studies on the Fauna of Curacao and Other Caribbean Islands,* 62(191): 1–173. The sample described in the paragraph above, differs from the published description of X. cf. wiedenmayeri in the possession of two categories of strongyles, with occasional tylote modifications, instead of the thick, oxeote spicules reported for X. cf. wiedenmayeri. Another difference is in the occurrence of this sponge in a deep reef environment; the specimen described in van Soest was reported to be taken from mangrove roots and muddy environments.

The extraction process is set forth below and in FIG. 1.

Isolation of CETP inhibitors from HRB-934

A portion of the frozen sponge (26 g) was lyophilized to give 7.2 g of freeze-dried sponge. The dry sponge was ground to a powder and extracted with petroleum ether for 24 hours using a soxhlet extractor. The extract was evaporated to dryness under vacuum using a rotary evaporator to yield 492 mg of residue. Column chromatography of 471 mg of the residue on silica gel employing gradient elution from heptane to 4:1 chloroform/heptane gave three CETP-active fractions. Analysis of the fractions by thin layer chromatography revealed that the first CETP-active fraction contained impure A, and the second CETP-active fraction contained pure A. Rechromatography of the first fraction employing identical conditions resulted in resolution of A, which when added to the pure A obtained from the first silica column, yielded a total of 25 mg of A. The third CETP-active fraction from the first silica column was subjected to further chromatography using silica gel and a step gradient beginning with 1:1 chloroform/heptane and continuing to 100% chloroform, and finally 1:9 methanol/chloroform.

This gave one CETP-active fraction which was found to be pure B (25 mg).

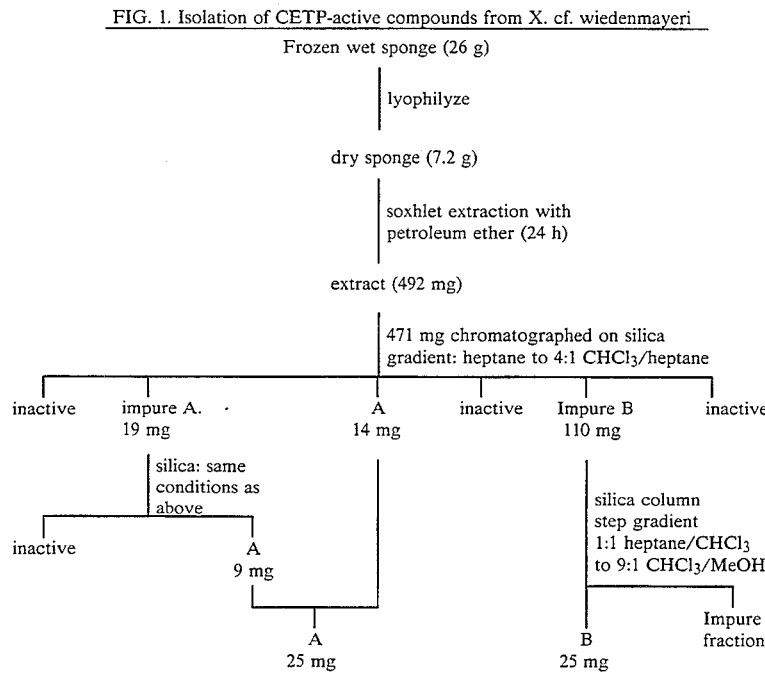

FIG. 1. Isolation of CETP-active compounds from X. cf. wiedenmayeri

Compounds A and B have the physico-chemical characteristics set forth in tables 1,2 and 3 below.

TABLE 1

Physico-chemical properties of Compounds A and B

| Spectral Method | Compound A | Compound B |
|---|---|---|
| UV (heptane) $\lambda_{max}$ (e) | 201 (17700), 288 (640) | 199 (41400), 288 (16100), 325 (9400) |
| IR (film) cm$^{-1}$ | 3498 br, 3340, 2945, 1615, 1492, 1288, 1385, 1258, 1181, 1085, 789, 728 | 3500 br, 2934, 1596, 1498, 1466, 1377, 1316, 1258, 1208, 1155, 758 |
| $[\alpha]_D^{21.5}$ (chloroform) | +121.0° | −40.5° |
| High resolution peak matching by FAB MS for the (M + H)$^+$ peak: | calculated: 345.2430 observed: 345.2410 | calculated: 345.2430 observed: 345.2413 |
| Major chemical ionization mass spectral peaks: m/z (relative abundance) | 345 (39), 344 (15), 191 (38), 153 (100) | 345 (38), 344 (58), 191 (53), 153 (100) |

TABLE 2

$^1$HNMR Chemical Shift Assignments*

| H-# | Compound A δ(ppm) J(Hz) | Compound B δ(ppm) J(Hz) |
|---|---|---|
| 7 | 2.16 2H dd 8.9, 4.3 | |
| 8 | | |
| 11 | 0.86 3H s | 0.91 3H s |
| 12 | 1.03 3H s | 0.91 3H s |
| 13 | 0.86 3H s | 1.25 3H s |
| 14 | 1.72 3H s | 1.03 3H d 7.6 |
| 15a | 3.46 2H ABq 17.2 | 5.78 1H s |
| 15b | 3.46 2H ABq 17.2 | — |
| 4' | 6.69 1H d 8.8 | 6.76 1H d 8.8 |
| 5' | 6.30 1H d 8.8 | 6.36 1H d 8.8 |
| OMe | 3.77 3H s | 3.70 3H s |
| OH | 7.48 1H s | 5.13 1H s |
| OH | 5.14 1H br s | 4.97 1H s |

*Assignments based on HETCOR and SINEPT Correlations. As used herein, SINEPT means Selective Insensitive Nuclei Enhanced Through Polarization Transfer; and HETCOR means Heteronuclear correlation.

TABLE 3

$^{13}$CNMR Chemical Shift Assignments*

| C# | δCompd A | δCompd B |
|---|---|---|
| 1 | 35.9 t | 38.8 t |
| 2 | 18.8 t | 18.8 t |
| 3 | 41.6 t | 42.0 t |
| 4 | 33.5 s | 34.0 s |
| 5 | 51.7 d | 55.1 d |
| 6 | 18.8 t | 17.8 t |
| 7 | 33.6 t | 34.2 t |
| 8 | 133.1 s | 32.0 d |
| 9 | 143.7 s | 164.3 s |
| 10 | 39.6 s | 41.3 s |
| 11 | 33.3 q | 33.4 q |
| 12 | 21.8 q | 22.8 q |
| 13 | 20.0 q | 21.9 q |
| 14 | 20.6 q | 21.8 q |
| 15 | 24.8 t | 112.6 d |
| 1' | 113.6 s | 114.8 s |
| 2' | 140.3 s | 139.7 s |
| 3' | 139.1 s | 137.8 s |
| 4' | 110.8 d | 109.7 d |
| 5' | 101.5 d | 102.7 d |
| 6' | 150.7 s | 151.0 s |
| OMe | 55.9 q | 56.0 q |

*Assignments based on HETCOR and SINEPT data, and comparison of these data to those reported in J. Org. Chem. 1986, 51, 4568–4573.

Based on the foregoing data, the structures shown below were assigned to the compounds A and B.

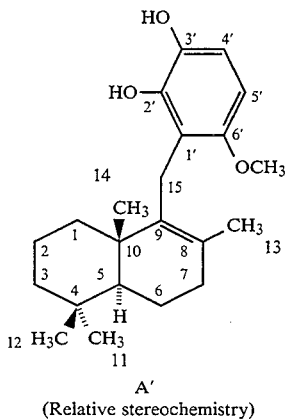

A'
(Relative stereochemistry)

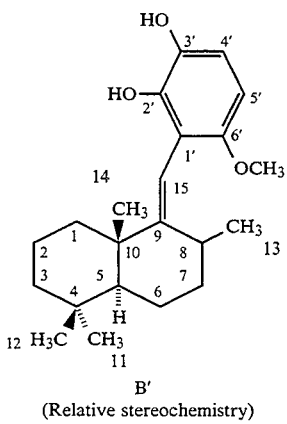

B'
(Relative stereochemistry)

It is pointed out that the absolute stereochemistry for the above two compounds has not been determined, only the relative stereochemistry. Thus, for example, compound A may have the structure shown just above, or it may have the structure

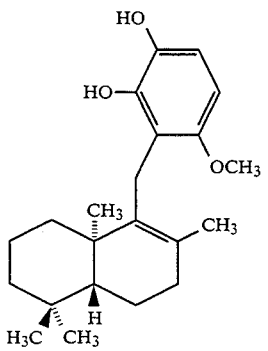

Either one or the other of the above enantiomers of A is extracted from X. cf. wiedenmayeri but not both.

Similarly, compound B may have the structure shown above, or it may have the structure

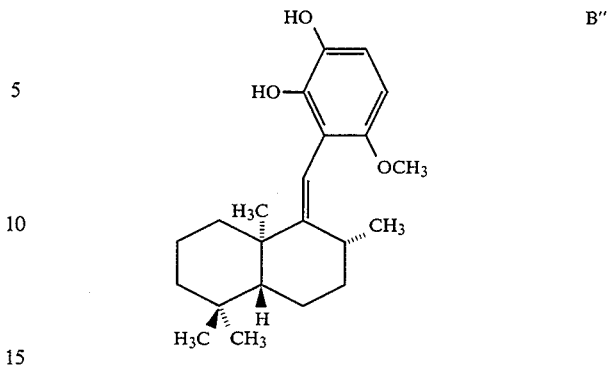

Either one or the other of the above enantiomers of B is extracted from X. cf. wiedenmayeri, but not both.

The compounds of the invention may form pharmaceutically acceptable salts with organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected from chloroprocaine, procaine, piperazine, glucamine, N-methylglucamine, N,N-dimethyl glucamine, ethylenediamine, diethanolamine, diisopropylamine, diethylamine, N-benzyl-2-phenylethylamine, N,N' dibenzyl-ethylenediamine, choline, clemizole, tris(hydroxymethyl) aminomethane, or D-glucosamine. The suitable inorganic bases include alkali metal hydroxides such as sodium hydroxide.

The following assay method was used to illustrate the biological activities of the compounds of the invention.

CETP ASSAY PROCEDURE

This assay used a commercially available CETP Scintillation Proximity Assay kit (Amersham TRKQ7015). In this assay, the transfer of [$^3$H]cholesteryl esters from high density lipoprotein (HDL) to biotinylated low density lipoproteins (LDL) was measured following incubation of donor and acceptor particles in the presence of recombinant CETP (rCETP; see Wang S. et al J. Biol. Chem. (1992) 267:1746-17490 which is herein incorporated by reference). Following incubation, the reaction was terminated and transfer was measured in a single step addition of streptavidin SPA beads, formulated in an assay terminal buffer (Amersham). The rate of increase in signal was proportional to the transfer of [$^3$H]cholesteryl ester by CETP.

To 96-well microtiter plates (DYNATECH Microlite) was pipetted 5 $\mu$l of sample (or buffer for blank) of appropriate dilution. For example, 5 $\mu$l of 20 $\mu$M compound A (IC$_{50}$ for A=2 $\mu$M) gave approximately 50% inhibition of transfer activity. The IC$_{50}$ for compound B=2.9 $\mu$M. As a control, 5 $\mu$l of CETP monoclonal antibody TP-1, 1:10 dilution from ascites was added. The reaction was started by adding 45 $\mu$l of the following mixtures to each well.

20 $\mu$l of assay buffer (from kit)
10 $\mu$l $^3$H]Cholesteryl ester-HDL (from kit)
10 $\mu$l of biotinylated LDL (from kit)
5 $\mu$l of rCETP The contents of the plate were mixed briefly by tapping the plate gently and then the plate was sealed with parafilm to prevent evaporation during the incubation. The plates were incubated at 37° C. for 4 hours. After incubation the reaction was stopped by adding 200 μl of streptavidin beads to each well. The beads were shaken gently before addition. The mixture was incubated at room temperature for 30 minutes to allow the assay to come to equilibrium with beads. Dpm were counted on a TopCount (Packard Instrument Company, Downers Grove, Ill.) (A conventional scintillation counter with window settings fully open may also be used).

Based upon the foregoing biological data, it can be concluded that the compounds of the invention are useful as agents in the treatment of dyslipidemia. It can be concluded that the compounds of the invention are useful as anti-fertility agents for mammals.

In accordance with the invention, pharmaceutical compositions comprise, as the active ingredient, an effective amount of a compound of the formula A or B, and one or more non-toxic, pharmaceutically acceptable carriers or diluents. Examples of such carriers for use in the invention include ethanol, dimethylsulfoxide, glycerol, silica, alumina, starch equivalent carriers and diluents.

While effective amounts may vary as conditions in which such compositions are used may vary, a minimal dosage required for therapeutic activity is generally between about 1 and about 1000 milligrams, 1 to 4 times daily.

The compounds may be administered as a tablet, a capsule, solution, suspension or an aerosol. It may be administered orally, subcutaneously, intravenously, topically or by inhalation.

Therapeutic applications can be contemplated to be accomplished by any suitable therapeutic method and technique presently, or prospectively known to those skilled in the art.

What is claimed is:

1. A compound of the formula:

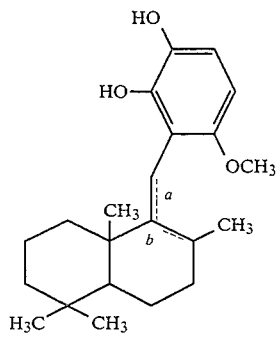

wherein a is a single bond and b is a double bond; or a is a double bond and b is a single bond; and enantiomers thereof; or a pharmaceutically acceptable salt thereof.

2. The compound in accordance with claim 1 which has the structural formula

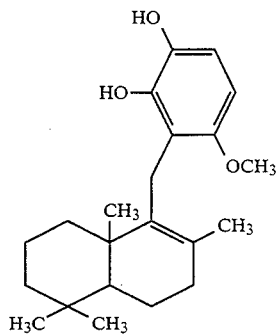

an enantiomer, or a pharmaceutically acceptable salt thereof.

3. The compound in accordance with claim 1 which has the structural formula

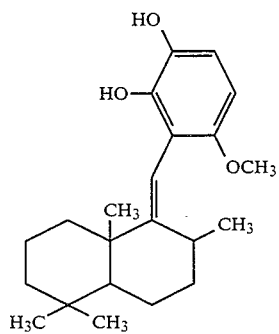

an enantiomer, or a pharmaceutically acceptable salt thereof.

4. A pharmaceutical composition comprising an effective amount of a compound of claim 1 and a pharmaceutically acceptable carrier material.

* * * * *

UNITED STATES PATENT AND TRADEMARK OFFICE
CERTIFICATE OF CORRECTION

PATENT NO. : 5,446,207
DATED : August 29, 1995
INVENTOR(S) : Shirley A. Pomponi, Vincent P. Gullo, Ann C. Horan, Mahesh G. Patel, Stephen J. Coval It is certified that error appears in the above-indentified patent and that said Letters Patent is hereby corrected as shown below:

Column 2: lines 54-55: "wiedendiol-A (A) and wiedendiol-B (B)." should read --wiedendiol-A (A) and wiedendiol-B (B).--.

Column 3: line 8: "CasteIII" should read --Castelli--; line 29: "Agelion" should read --Agellon--.

Column 4: lines 18-19: "Insland" should read --Island--; line 22: "lefe" should read --life--; lines 22-23: "in ethanol. it is" should read --in ethanol, it is--; line 33: "Xestosoongia cf. wiedenmaveri" should read --Xestospongia cf. wiedenmayeri--.

Column 8: line 43: "267:1746-17490" should read --267:1748-17490--; line 67: "parafiim" should read --parafilm--.

Signed and Sealed this

Nineteenth Day of March, 1996

Attest:

BRUCE LEHMAN

Attesting Officer     Commissioner of Patents and Trademarks